United States Patent [19]

Guirguis

[11] Patent Number: 5,244,815
[45] Date of Patent: Sep. 14, 1993

[54] FINGERPRINT TEST PAD AND METHOD FOR FINGERPRINTING USING PARTICLE BASED IMMUNOASSAY

[75] Inventor: Raouf A. Guirguis, Rockville, Md.

[73] Assignee: LaMina Ltd., Rockville, Md.

[21] Appl. No.: 759,922

[22] Filed: Sep. 13, 1991

Related U.S. Application Data

[63] Continuation-in-part of Ser. No. 668,115, Mar. 12, 1991, which is a continuation-in-part of Ser. No. 467,532, Jan. 19, 1990.

[51] Int. Cl.$^5$ .................. G01N 33/545; G01N 33/94; G01N 33/553
[52] U.S. Cl. .................................. 436/530; 436/525; 436/531; 436/536; 436/538; 436/800; 436/810; 436/815; 436/816; 436/817; 436/901; 435/7.92
[58] Field of Search ............... 436/530, 531, 518, 534, 436/525, 536, 810, 815, 816, 901, 538, 808; 422/56, 57, 60; 435/975, 7.92

[56] References Cited

U.S. PATENT DOCUMENTS

| | | | |
|---|---|---|---|
| 4,632,901 | 12/1986 | Valkirs et al. | 435/5 |
| 4,774,192 | 9/1988 | Terminiello et al. | 436/530 |
| 4,853,335 | 8/1989 | Olsen et al. | 436/527 |
| 4,883,764 | 11/1989 | Kloepfer | 436/63 |
| 4,963,325 | 10/1990 | Lennon et al. | 422/61 |
| 5,009,919 | 4/1991 | Vassiliades | 427/1 |
| 5,079,172 | 1/1992 | Hari et al. | 436/518 |

FOREIGN PATENT DOCUMENTS 200381 11/1986 European Pat. Off. .

OTHER PUBLICATIONS

Alan J. Weiss and Larry A. Blankstein; "Membranes as a solid phase for clinical diagnostic assays"; *American Clinical Products Review*, Jun. 1987.

Primary Examiner—Esther L. Kepplinger
Assistant Examiner—Carol E. Bidwell
Attorney, Agent, or Firm—Leydig, Voit & Mayer

[57] ABSTRACT

A method and device for testing for the presence of substances such as drugs in body fluids while simultaneously positively identifying the test subject. The device comprises an absorbent pad and a membrane mounted to the absorbent pad containing a plurality of separated areas provided with different immobilized ligand having a specific receptor site for capture or rejection of specific antigens produced by different predetermined drugs. The method of testing comprises the steps of: (a) obtaining a quantity of body fluid in a container, (b) adding an antibody to the body fluid to form a mixed solution, (c) placing the mixed solution on a membrane and absorbent pad device and immobilized ligands, (d) covering the finger with a thin film of labelled antibody and (e) placing the finger on the membrane containing immobilized ligand specifically selected to bind to labelled antibody presenting the fingerprint of the test subject, the presence or absense of substances being tested for in the body fluid so that solution is deposited from the finger on the membrane indicating presence or absence of the substance.

43 Claims, 11 Drawing Sheets

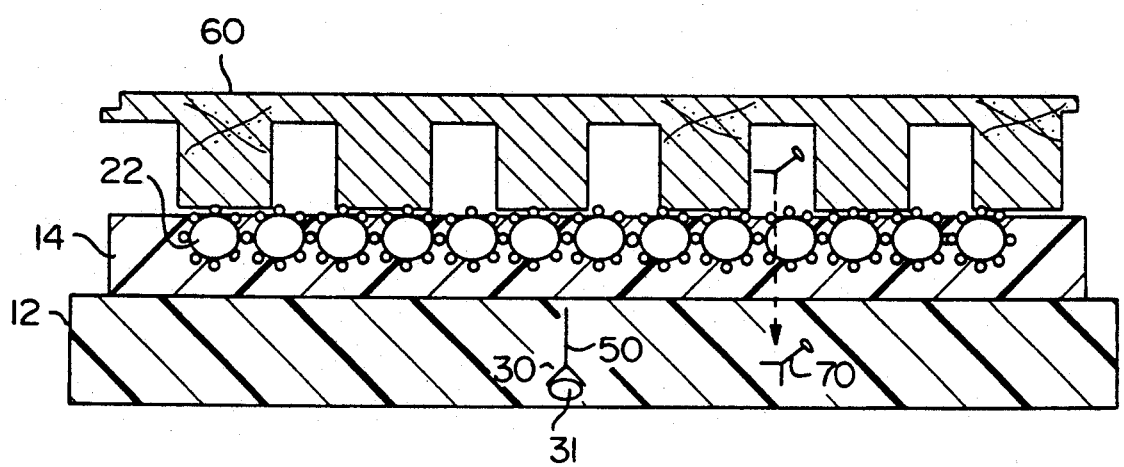
FIG. 12
FIG. 13
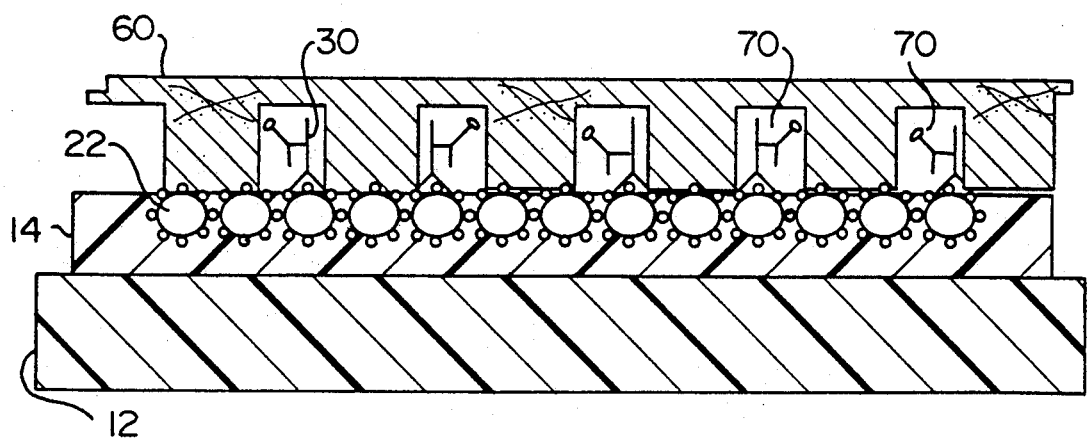

FINGERPRINT TEST PAD AND METHOD FOR FINGERPRINTING USING PARTICLE BASED IMMUNOASSAY

RELATED APPLICATIONS

This is a continuation-in-part application of U.S. patent application Ser. No. 07/668,115 filed Mar. 12, 1991 which is a continuation-in-part of U.S. patent application Ser. No. 07/467,532 filed Jan. 19, 1990.

BACKGROUND OF INVENTION

The present invention is directed to an individual testing method and device and more specifically to a method and device for detecting the presence of specific antigens or specific antibodies produced by drugs in a biological fluid such as saliva, urine or blood and using the device to also positively identify the individual tested by reproducing the fingerprint of the person being tested. Previously drug testing has been accomplished by testing individual fluid samples such as urine or blood to determine the presence of drugs in the body. Such testing procedures are very common in the athletic world (Table I), prisons, courts of law, and in the general workplace and are many times prescribed by contracts between the individual and his/her employer or labor union which represents the individual or group. A problem which has occurred during such testing is that test fluids are obtained from persons other than the person to be tested or that test fluids become mixed, lost, or cannot be specifically identified with that person after the test comes back with positive results. Another problem is that the time for testing is generally too long to obtain results which are timely.

The present invention attempts to overcome the problems which are inherent in the prior art through the use of a specifically designed fingerprint pad device which tests for the presence of drugs or other specified agents in the body fluids as well as providing an inkless (immunoassay-based) fingerprint of the person giving the test sample so that positive identification of the fluid donor is irrefutably obtained.

Theory and Design of Immunoassays

The family of immunoassays works upon the single principle that is the specific recognition of an antigen by an antibody. The specific antigen detection and quantification requires an antibody which recognizes the uniqueness of an antigen. One unique binding site on the antigen site serves as an identifying marker for an antibody, which is typically a protein.

Thus, detection can be direct where the antigen-specific antibody is purified, labelled and used to bind directly to the antigen or indirect where the antigen-specific antibody is unlabelled and need not be purified. In indirect detection the binding to the antigen is detected by a secondary reagent, such as labelled anti-immunoglobulin antibodies or labelled protein A. A variation that uses aspects of both the direct and indirect methods modifies the primary antibody by coupling to it a small chemical group such as biotin or dinitrophenol (DNP) so that the modified primary antibody can then be detected by labelled reagents such as a biotin binding protein or haptene-specific antibodies such as anti-DNP antibodies.

Solid-Phase Immunoassay

The design of immunoassays for the detection and quantification of biomolecules in a mixture of cross-reactive molecules can differ from that intended to detect smaller molecules such as hormones and drugs. Antibodies which are immobilized (irreversibly bound) on a membrane are well known in the art and such antibodies are designed to have binding sites which have high affinity for the epitopes of the antigens carried in the saliva and vice versa. Covalent binding of protein to the membrane surface offers a permanent bond which is irreversible, so that once a protein, like an antibody, is bound, it will not be desorbed during an assay.

The principle of affinity chromatography requires that a successful separation of a biospecific ligand is available and that it can be chemically immobilized on a chromatographic bed material, the matrix. A number of methods which are well known in the art have been used to couple or immobilize the ligand to a variety of activated resins.

Examples of immobilization techniques which exhibit variable linkage are those formed by the reaction of the reactive groups on the support with amino, thiol, hydroxyl, and carboxyl groups on the ligand protein. The selection of the ligand or antibody is influenced by two factors. First, the ligand should exhibit specific and reversible binding affinity for the substance to be purified and secondly it should have chemically modifiable groups which allow it to be attached to the matrix without destroying its binding activity. (Examples of such are Protein G manufactured by Pharmacia, Hydrazide AvidGel Ax manufactured by BioProbe International, and Actigel-ALD manufactured by Sterogene Bioseparation Inc.)

When a definitive antibody for a given antigen is available, it is used to identify the antigen in the sample mixture. Once the antibody combines with the antigen, a means is needed to recognize the complex. This has been accomplished in the past by providing a labelled antibody, such as an enzyme, enzyme link immunosorbent (ELISA) -type assay so that the site is incubated with a chromogenic substrate and a color is developed whose intensity is proportional to the enzyme label present.

Particle-Based Diagnostic Tests

Microspheres or uniform size particles are used in a wide variety of modern diagnostic tests and assays. Particle-based diagnostic test qualitative/quantitative assays are usually based upon the specific interaction of antigen and antibody. Antigen or antibody can be absorbed onto or bound to submicron size polystyrene (PS) particles, often called "uniform latex particles". These sensitized particles then act to magnify or amplify the Antigen-antibody reaction which takes place when a sample containing the sought molecule is mixed with these appropriately coated particles.

In the classic example, a positive test results when uniformly dispersed milky appearing antibody (Ab)-coated particles in a drop of water on a glass slide react with antigen (Ag) in a drop of sample (whole blood, serum, urine, etc.) to cause particle agglutination (coagulation or clumping). An improvement in Latex Agglutination Tests (LATs) is the use of dyed particles which provide different contrast (dyed particles observed against a white background). They also permit some tests using samples of whole blood, if dark blue or black particles are used. As an example of the versatility of dyed particles, Wellcome Diagnostics (Dartford, Kent, England) has a Salmonella test which uses anitbodies to three different antigen groups bound to three different colored particles (red, blue and green). By comparing the shade of the color of the combined agglutinated particles to a background color, one can decide which of seven combinations of Salmonella groups are present in the sample.

Enzyme Immunofiltration Assays (EIFA)

EIFA utilize microporous membranes as the receptor-bearing solid phase and employ filtration as a means to hasten contact with the soluble sample ligand and the signal generating reagents. To prepare these tests, Ab is absorbed onto PS particles; the particles are caught on a filter and dried. In use: First, a sample is passed through the filter and any Ag is caught by the Ab on the particles. Next, a second Ab-enzyme reacts with it to create an insoluble colored product which is proportional to the amount of Ag caught. The diffusion limitation of the reaction rate seen for conventional solid-phase immunoassays is minimized in EIFA. This is due to the flow of reactants through the receptor bearing membrane solid phase and the high ratio of microporous membrane surface area to liquid volume. Thus, EIFA permits rapid tests to be developed which reach completion in minutes. The antigen-antibody reactions in EIFA are visualized directly by immunostaining, in which the signal-generating conjugate yields colored spots at the reaction sites on the membrane. The color intensity of these spots can be quantitated by reflectance photometry.

Various EIFA methods have been described for the detection of antigens by means of direct binding of sample to the membrane or by employing two antibodies in a sandwich. Detection of antbodies by permutations of this method has also been described. In the sandwich assay described by Valkirs and Barton, rapid flow followed by a short incubation period was used to give a total assay time of 5 minutes. Quantitative assays based on EIFA have reproducibility and sensitivity comparable to that of other enzyme linked immunosorbent assay (ELISA) techniques. The EIFA system can be incorporated in a unit which, besides the antibody-bearing solid phase, includes an absorbing material for drawing liquid through the membrane and a waste reservoir. Because of their convenience, simplicity, and speed EIFA devices can be used in technically unsophisticated patient environments, i.e., as a near the patient test.

Various tests (like HCG, "strep" A, and others), using this principle have been made by Hybritech (ICON). Abbott (Testpack), Novo Nordisk A/S (NovoClone Target), and many others. Murex SUDS uses liquid reagents in their tests: mixing Ab-coated particles+Ag (from sample)+second Ab-enzyme conjugate; then pouring the mixture through their filter device to capture the particles which are rinsed with enzyme substrate to form color.

Filter Separation Agglutination Tests (Assays)

Kodak's earliest Surecell test kits used dyed agglutinated particles caught on a filter. Red dyed particles coated with Ab were incubated with a sample and poured on a filter. Single particles passed through the filter and no color appeared on the surface. If the sample contained the appropriate Ag, the particles agglutinated and the agglutinated clumps were caught upon the filter resulting in a red (or pink) positive color test for the Ag. This principle could easily be applied to an assay procedure where the reflected color intensity would correlate with the sample's Ag content. Costar Corp. has proposed a particle agglutination capture ELISA scheme. After reaction with chromogenic substrate, soluble substrate is measured in a spectrophotometer (microplate reader).

Improved Dyes and Latexes

Small microspheres with bright, photostable fluorescent or colored dyes have opened up major new opportunities for sensitive diagnostic tests. Fluorescent latex is inexpensive and widely applicable to qualitative and quantitative immunodiagnostics. The uses of fluorescent latex particles should be applicable to most, if not all of the major latex-based diagnostic test systems presently in use, including latex agglutination tests (LAT), filter separation tests (in which agglutinated particles are trapped on a filter), particle capture ELISA methods and two-particle sandwich techniques. The increased signal available from fluorescence offers the option of quantitative, as well as qualitative results, with potential sensitivity increases of over 1000-fold, compared to colorimetric methods.

Saliva Collection and Drugs of Abuse Testing

Saliva is a transcellular fluid produced by several paired salivary glands, particularly the parotid, the submaxillary, the sublingual glands and some other small glands.

Since almost all drugs are not naturally present in the body, the detection of such drugs in the test subject body fluid will indicate the use of these drugs by the subject. The measurement of a drug in saliva has been suggested to estimate the free, pharmacologically active concentration of the drug in serum. There is, however, a considerable difference in pH between saliva and serum, and ratios of bound drug to free drug would have to be normalized to the serum values.

It is known that there is a correlation between cocaine levels in blood and levels of cocaine in saliva Vol 11, *Journal of Analytical Toxicology*, p. 36, January/February 1987) and that cocaine can be found in saliva after cocaine administration in concentrations equal to or greater than those in plasma allowing for the possibility of a relatively noninvasive means of cocaine detection and monitoring (Vol. 34, *Clinical Chemistry*, p. 150B, No. 7, 1988). It is also known that detection of cocaine in saliva and urine is successful through the first 24 hours of collection for saliva and 4-5 days for urine (Vol. 13, *Journal of Analytical Toxicology*, p. 65, March/April 1989.

Furthermore, it has been proposed that morphine and codeine usage can be found in testing human hair long after drug levels in urine, plasma and saliva are not detectable and a comparison of same with drug levels in biofluids is found in Vol. 14, *Journal of Analytical Toxicology*, p. 1, January/February 1990.

Medium dosages of heroin in the range of 5-10 mg per 70 kg has been found detectable in saliva 1 to 2 hours after use as was dextromethorphan, while morphine has been found detectable for 3 to 4 hours after the last morphine dose. (Vol. 15, *Clinical Pharmacology and Therapeutics*, p. 579, No. 6, 1974).

A saliva collection device for the quantitative determination of endogenous substances and therapeutic drugs is disclosed in Vol. 37, *Clinical Chemistry*, pp. 114-115, No. 1, 1991. The saliva is collected in the buccal cavity by a specially designed device comprising an osmotically active substance enclosed in a pouch consisting of a semipermeable membrane to form a disc of about 35 mm diameter.

Drug testing has been part of major international athletic competitions. The non-medical uses of drugs for athletic performance has been banned by the International Olympic Committee (IOC) for several years. A list of the banned drugs during the 1988 Olympic Winter Games in Calgary was published in Vol. 37, Clinical Chemistry p. 1289, No. 7,1991, table i. A fair number of the drugs listed are known to be secreted in saliva as well as in urine.

It is, therefore, desirable to provide an easy to handle disposable testing pad which holds a composite saliva, blood or urine sample mixed with specific antibody selected to capture specific antigens. A finger of the test subject is coated with a labelled antibody and the finger is pressed on a membrane substrate having a specific immobilized antibody or antigen bed to capture a concentrated amount of specified antigen and/or labelled antibody from the body fluid while simultaneously providing an inkless (immunoassay-based) color fingerprint of the testee so that positive identification of the fluid donor is irrefutably obtained. The fingerprint of the fluid donor obtained on the membrane should also include information about the status of the drugs present in his body fluids at the time of performing the test. This information can be recorded or stored for positive identification when needed.

TABLE I

β-Blockers
Acebutolol
Alprenolol
Atenolol
Labetalol
Metoprolol
Nadolol
Oxprenoiol
Propranolol
Sotalol and related compounds
Diuretics
Acetazolamide
Amilonde
Bendroflumethiazide
Bumetanide
Canrenone
Chlormerodrin
Chlorthalidone
Diclofenamide
Ethacrynic acid
Furosemide
Hydrochlorothiazide
Mersalyl
Spironolactone
Triamterene and related compounds
Stimulants
Amfepramone
Amphetamine
Amphetaminil
Amiphenazole
Benzphetamine
Caffeine
Cathine
Chlorphentermine
Clobenzorex
Clorprenaline
Cocaine
Cropropamide
Crotethamide TABLE I-continued Dimethamphetamine
Ephedrine
Etafedrine
Ethamivan
Etilamphetamine
Fencamfamin
Fenethylline
Fenproporex
Furfenorex
Mefenorex
Methamphetamine
Methoxyphenamine
Methylephedrine
Methylphenidate
Morazone
Nikethamide
Pemoline
Pentetrazol
Phendimetrazine
Phenmetrazine
Phentermine
Phenylpropanolamine
Pipradrol
Prolintane
Propylhexedrine
Pyrovalerone
Strychnine and related compounds
Narcotic analgesics
Alphaprodine
Anileridine
suprenorphine
Codeine
Dextromoramide
Dextropropoxyphene
Diamorphine
Dihydrocodeine
Dipipanone
Ethoheptazine
Ethylmorphine
Levorphanol
Methadone
Morphine
Nalbuphine
Pentazocine
Pethidine
Phenazocine
Trimeperidine and related compounds
Anabolic steroids
Bolasterone
Boldenone
Clostebol
Dehydromethyltestosterone
Fluoxymesterone
Mesterolone
Methandienone
Methenolone
Methyltestosterone
Nandrolone
Norethandrolone
Oxandrolone
Oxymesterone
Oxymetholone
Stanozolol
Testosterone and related compounds

SUMMARY OF THE INVENTION

The invention is directed a body fluid, antigen/antibody-containing collection device and method for testing and fingerprint identification. The device is in the form of a support member with an absorbent section having a permeable membrane test pad mounted thereon which is coded with specific zones containing embedded antigen coated particles and antibody coated particles to capture or preclude capture of specific antigens carried by the fluid to determine the presence in the body of specific drugs or substances. It is, of course, apparent that antigens and antibodies can be switched and either immobilized to capture the other.

It is an object of the invention to collect antigen and/or antibodies from fluid samples removed from the body for testing while simultaneously obtaining a fingerprint pattern through the pressing of labelled antibody with the coated finger of the test subject against the fluid sample covered pad to positively identify the donor of the sample. Previously such testing has been accomplished by a series of tests which may involve shifting of the fluid being tested to different containers and removal of the fluid from the person being tested to a place distant from the person which allows fluid misplacement and substitution and questions as to the chain of title of the tested fluid.

It is also an object of the invention to segregate various areas of the pad and provide specific immobilized antibodies which react to specific drugs or substances on different predetermined separated areas so that a multiple drug test can be given to the test subject.

In the accompanying drawings there is shown an illustrated embodiment of the invention from which these and other objectives, novel features and advantages will be readily apparent.

BRIEF DESCRIPTION OF THE DRAWINGS

FIG. 12 is an enlarged schematic cross sectional representation across a test area of the finger pad of the present invention following FIG. 11 when antigen is present showing the action of the anti-mouse antibody passing through the membrane, uncaptured by the antigen immobilized on particles embedded in the membrane, onto the absorbent area of the pad;

FIG. 13 is an enlarged schematic cross sectional representation across a test area of the finger pad invention of the present following FIG. 11 when antigen is absent showing the colloidal gold goat anti-mouse antibody captured by mouse antibodies immobilized on the antigen-coated particles of the membranes;

DETAILED DESCRIPTION OF THE INVENTION

The best mode and preferred embodiment of the invention is shown in FIGS. 1-15. The present invention is directed to a fingerprint pad testing apparatus 10 and to a method of conducting a test using such apparatus.

Figure 1:
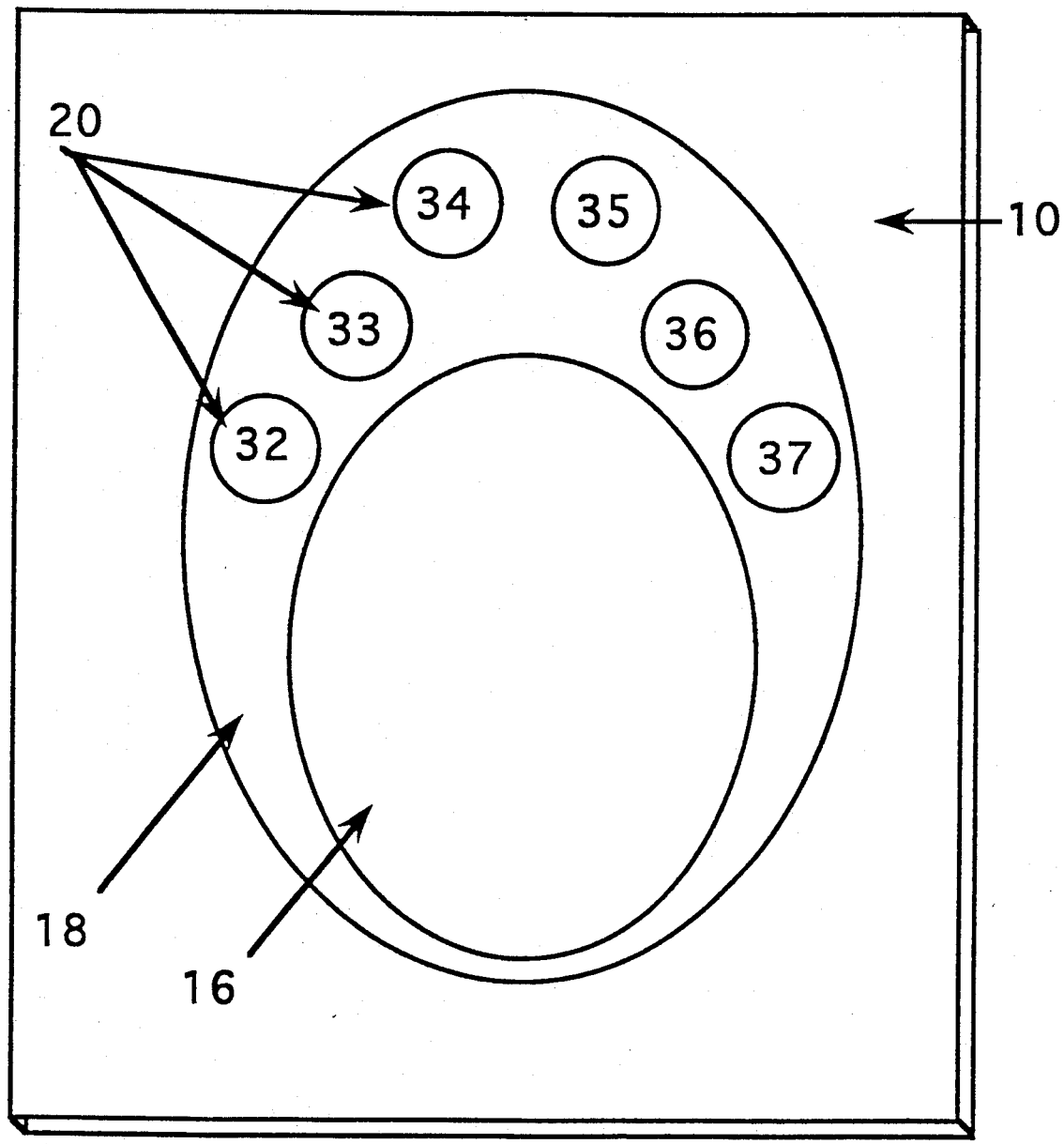
FIG. 1 is a plan view of the fingerprint test pad of the present invention.
Figure 2:
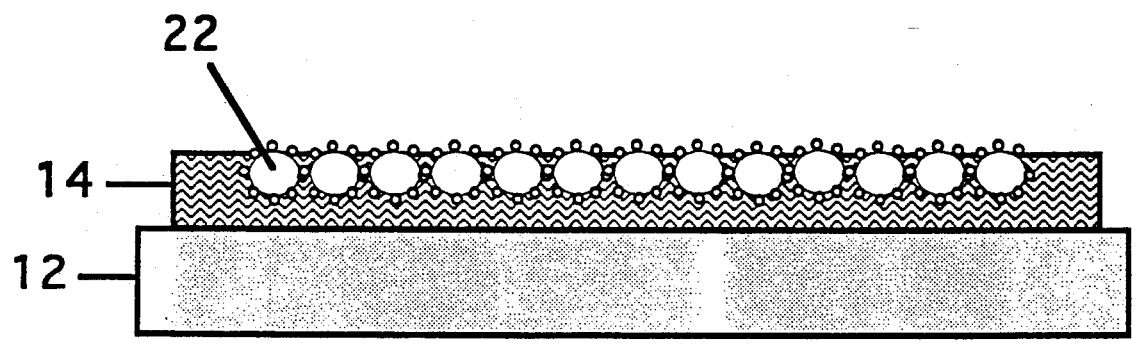
FIG. 2 is an enlarged schematic cross sectional view taken across a test area of the fingerprint test pad shown in FIG. 1 showing antigen coated particles embedded in the pad membrane.
Figure 3:
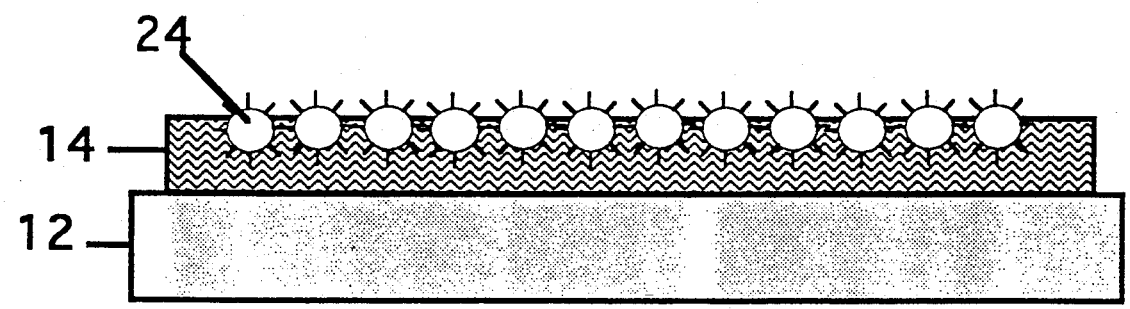
FIG. 3 is an enlarged schematic cross sectional view taken across a control area of the fingerprint test pad shown in FIG. 1 showing goat anti-mouse antibody coated particles embedded in the pad membrane.
Figure 4:
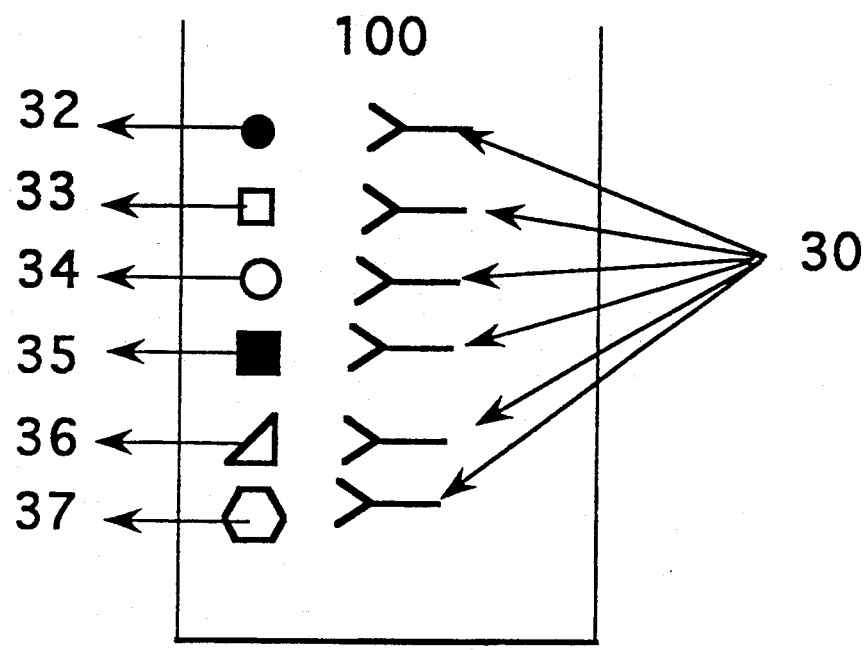
FIG. 4 is a schematic representation of a body fluid test sample having various analytes in the sample mixed with mouse antibodies against the specific analytes.
Figure 15:
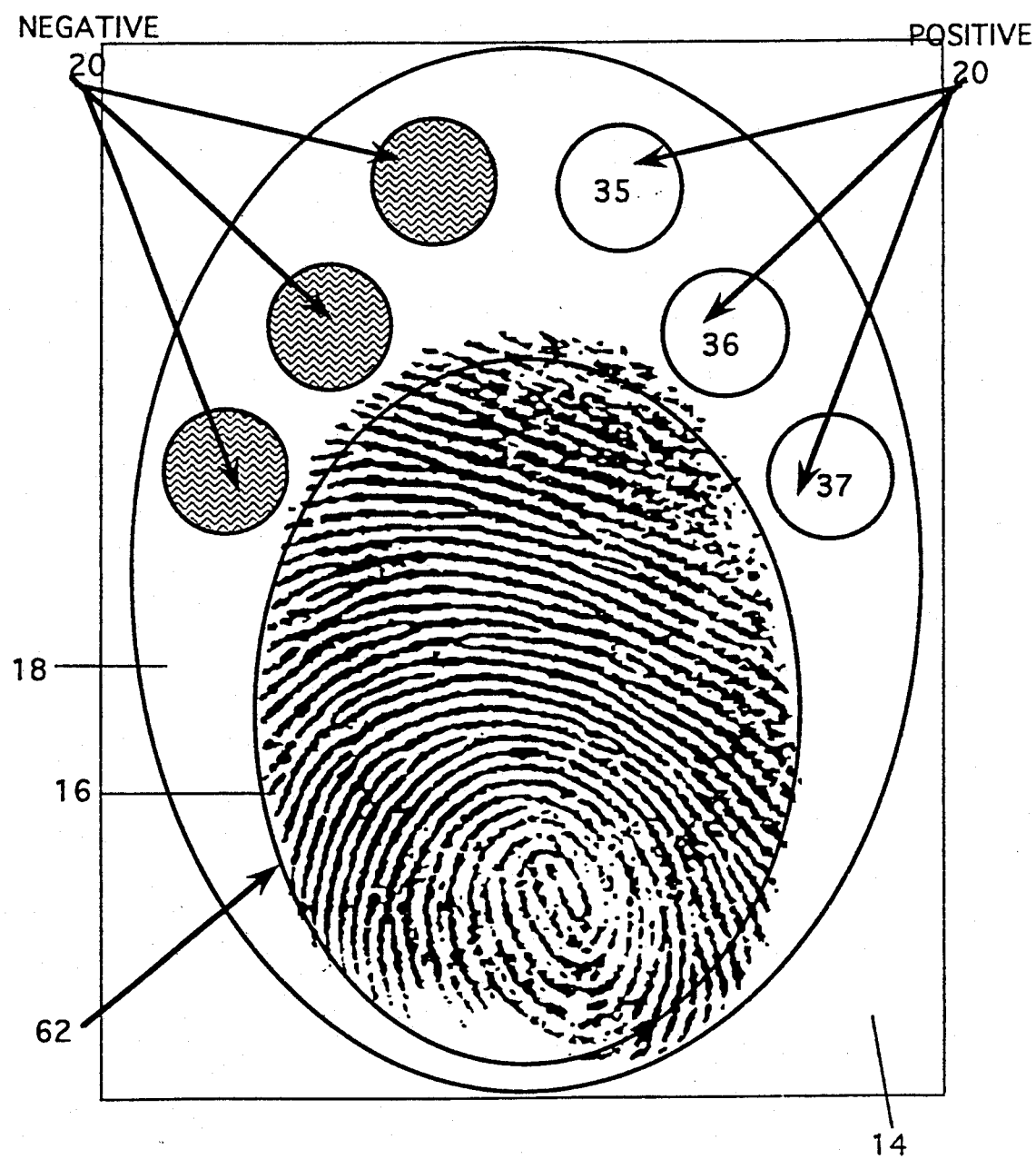
FIG. 15 is an enlarged representation of the test results on the fingerprint test pad in the test area and control area.

The apparatus 10 is constructed with a porous plastic absorbent base member 12 upon which is mounted a plastic membrane 14. The plastic membrane 14 is divided into a zone having elliptical control areas 16 and 18 and a zone having circular test areas 20. The test areas 20 are constructed with antigen coated polystyrene particles 22 embedded in the membrane and the control areas 16 and 18 are constructed with mouse anti-goat antibody coated polystyrene particles 24 embedded in the membrane. A schematic cross section of the test and control areas is shown in FIGS. 2 and 3, respectively. In the invention the subject test body fluid sample 100 is mixed in container 40 with unlabelled mouse antibodies 30 which are specifically selected to have receptor sites to capture different analytes (antigen) 32, 33, 34, 35, 36 and 37, as shown in FIG. 4. The mouse antibodies 30 against the different analytes are premixed with the body fluid 100 and the mouse antibodies complex with the antigen(s) in the body fluid 100 prior to applying as the mixed solution 102 to membrane 14. After incubation of the mixed solution on the membrane, a labelled goat anti-mouse antibody 70 is painted on the fingertip 60 and is pressed against the membrane 14 to produce the fingerprint 62 (FIG. 15). The membrane 14, which is preferably of a low protein binding type with polystyrene particles entrapped on its surface has a planar surface, which, as shown in FIG. 1, is divided up into separate circular test areas 20 which are provided with immobilized ligands which, while described as antigen coated particles, can take the form of antibodies or antigens coated on particles which in turn attach to predetermined ligands carrying specific substances. The test segment areas are shown reacting or holding molecules of cocaine 32, opiates 33, PCP 34, amphetamine/methamphetamine 35, marijuana 36 and alcohol 37 although other substances can be substituted.

An index of the various drugs which can be tested using the present invention is as follows:

| STIMULANTS | HALLUCINOGENS |
|---|---|
| Cocaine | Lysergic Acid |
| Amphetamine | Diethylamide |
| Methamphetamine | Mescaline |
| Methylphenidate | Phencyclidine P.C.P. |
| Phenmetrazine | Ketamine |
| Phenylpropanolamine | 2,5-Dimethocy-4-Methylamphetamine |
|  | Tetrahydrocannabinol |
|  | Marijuana |
| OPIATES | SEDATIVES/HYPNOTICS |
| Heroin | Cholral Hydrate |
| Morphine | Glutethimide |
| Methandone | Meprobamate |
| Meperidine | Methaqualone |
| Codeine |  |
| Propoxyphene |  |
| BARBITURATES | BENZODIAZEPINES |
| Amobarbital | Diazepam |
| Pentobarbital | Clorazepate |
| Secobarbital | Chlordiazepoxide |
| Phenobarbital | Oxazepam |
| Butalbital | Flurazepam |
| Butabartial | Lorazepam |
|  | Alprazolam |
| ANTIPSYCHOTICS/ ANTIDEPRESSANTS | SOLVENTS |
| Chlorpromazine | Ethanol |
| Trazodone | Methanol |
| Haloperidol | Isopropanol |
| Amoxapine | Ethylene Glycol |
| Lithium Carbonate | Chloroform |
| Imipramine |  |
| ANALGESICS | ANABOLIC STEROIDS |
| Acetylsalicylic | Testosterone |
| Acetaminophen | Methyltesiosterone |
| Ibuprofen | Nandrolone |
| Diflunisal | Stanozolol |
| Phenylbutazone | Oxandrolone |
|  | Methandrostenolone |
|  | Clostebol |
|  | Mesterolone |
|  | Norethandrolone |

Presence of one or more of the aforenoted drugs or predetermined substances in the body fluid provides the corresponding test segment or area segment with a negative, i.e., no color or inhibition assay. The body fluid sample 100 and mouse antibodies 30 are incubated for 3 minutes allowing the same to complex and the composite sample 102 is then dispensed from the container 40 into the center of the fingerprint pad 10. The composite sample 102 is allowed to sit on the pad 10 and incubate for two minutes and then is drained. A washing solution, not shown, is flushed over the surface of the membrane 14 and allowed to drain.

Figure 7:
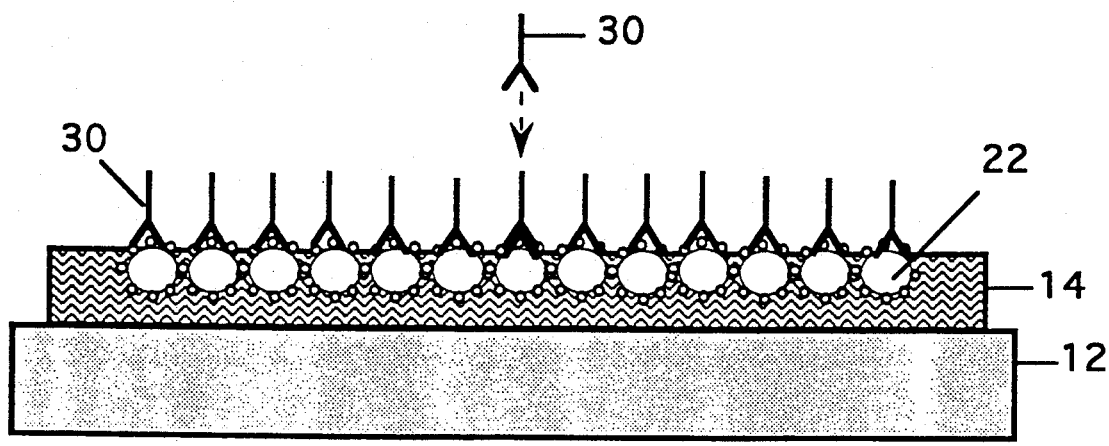
FIG. 7 is an enlarged schematic cross sectional view taken across the test area of the fingerprint pad of the present invention illustrating the absence of antigen in the composite sample and showing the antigen coated particles embedded in the membrane immobilizing the antibody on the surface of the membrane.
Figure 8:
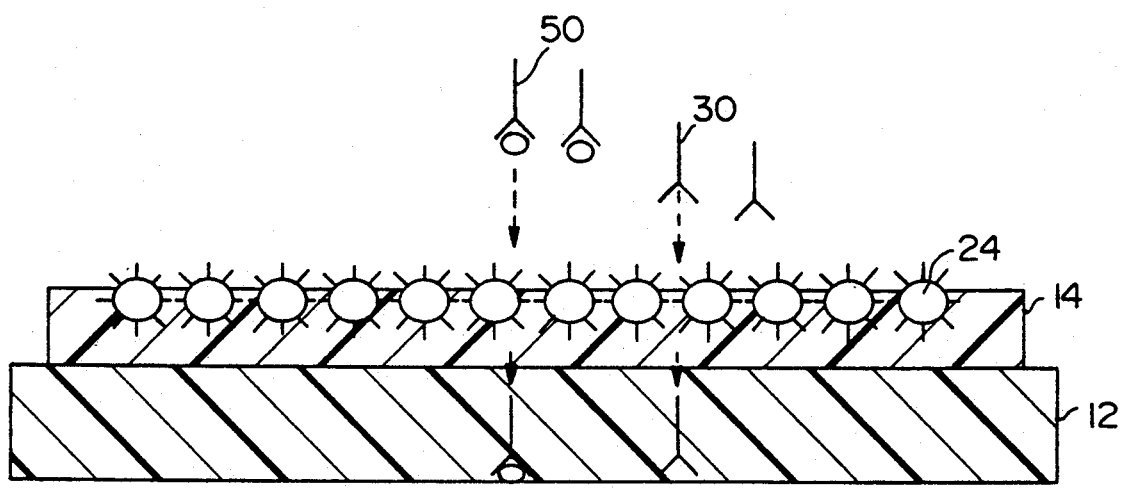
FIG. 8 is an enlarged schematic cross sectional view taken across a control area of the fingerprint pad invention illustrating that mouse anti-goat antibody coated particles embedded in the membrane control areas will not capture the primary anti-mouse antibodies.

If the test for antigens indicates a presence of predetermined antigen (32-37) in the test sample as shown in FIG. the antigen coated particles 22 embedded in the membrane 14 on the test areas will not capture the unlabelled mouse antibody 30 as the antibody 30 captures antigen 31 to form a complexed mouse antibody and captured antigen 50 which flows into the porous plastic pad 12 and is trapped there. If the test for antigens indicates an absence of predetermined antigen 31 from the test sample, as shown in FIG. 7, the antigen coated particles 22 embedded in the membrane 14 in the test area 20 will capture the unlabelled mouse antibody 30 on the surface of membrane 14. When the test sample is placed on the control areas 16 and 18 of the membrane 14, as illustrated in FIG. 8, the mouse anti-goat antibody coated particles 24 embedded in the membrane 14 on the control areas 16 and 18 will not capture the primary mouse antibodies 30 or the complexed mouse antibody/antigen 50 which will pass through membrane 14 and do not become entrapped on its surface.

The fingertip 60 of the user is then painted with 20 microliters of goat anti-mouse antibody labelled with colloidal gold 70. The fingertip 60 with labelled anti-mouse antibody 70 is lightly pressed against the membrane 14 and preferably held for 5 seconds, or within a range of 2-10 seconds, with the fingertip 60 then being removed from the membrane 14 of fingerprint pad. The anti-mouse antibody 70 is provided with microsphere labelling which colors the fingerprint in negative or reverse order of a normal print in that the valleys contain a majority of colloidal particles. The chromogenic substrate provides a detection for the antigen/antibody complex and the color produced is proportional to the amount of the unknown in the sample.

The preferred substrate used in the present invention is that of colloidal gold. Gold is biologically inert and has very good charge distribution. It is now becoming widely available in many useful forms. Its detection can be enhanced using several silver deposition methods available commercially. Colloidal gold also can be detected easily in electron microscopy applications and can be prepared in discrete and uniform size ranges, permitting double-labelling experiments. Several commercial companies have introduced silver enhancement kits permitting development to be monitored by the naked eye. Colloidal gold particles bind tightly but not covalently to proteins at pH values around the protein's pI. Colloidal gold particles conjugated with a wide range of anti-immunoglobulin antibodies, protein A or streptavidin are available commercially. Because some of the bound protein may slowly dissociate from the gold particles, the colloid can be washed if desired before use to remove free protein.

Gold labels give higher resolution than enzyme-based methods and avoid the problems of substrate preparation and endogenous enzyme activity. Until recently the gold labels lacked sensitivity at the level of light microscopy, but the recent development of the photochemical silver method of amplification has overcome this problem.

With the silver enhancement method, the gold particles become coated in metallic silver and yield a black-brown label, best visualized by bright-field optics. Gold labelling methods are compatible with many histochemical strains. Gold labelling reactions are very readily controlled, as the appearance of staining can be monitored directly with the naked eye. If the designated antigen 31 is present, the colloidal gold goat anti-mouse antibody 70 will pass through the test areas 20 of the membrane 14 onto the porous plastic absorbent pad 12 and become trapped therein as there are no receptor sites present on the membrane 14.

If the designated antigen 31 is absent, the colloidal gold goat anti-mouse antibody 70 will be captured by the mouse unlabelled antibodies 30 which have previously been captured by the antigen on the antigen particles 22 immobilized in the membrane 14 as is shown in FIG. 13. In the control areas 16 and 18 of the membrane, the colloidal gold goat anti-mouse antibody 70 will be captured by the mouse antibodies immobilized on mouse anti-goat antibody coated particles 24 embedded in the membrane 14 to present a fingerprint image. Thus, it is apparent that the test result as shown in FIG. 15 shows the fingerprint impression 62 in the control areas as well as giving negative and positive testing for the various antigens being tested for.

While collodial gold substrate is preferred over other dyed particles or microspheres, a chromogenic substrate provides an alternate sensitive detection method for the enzyme conjugate. The following Table II sets forth chromogenic substrates yielding water-insoluble products that can be used in the invention in place of the colloidal gold substrate previously noted.

TABLE II

Chromogenic Substrates Yielding Water-Insoluble Products

| Enzyme | Substrate | Abbreviation | Starting Color | Final Color |
|---|---|---|---|---|
| Horseradish Peroxidase | Diaminobenzidene | DAB | Clear | Brown |
| | Diaminobenzidene with nickel enhancement | DAB/ nickel | Clear | Grey/ Black |
| | 3-Amino-9-ethylcarbazole | AEC | Clear | Red |
| | 4-Chloro-1-naphthol | — | Clear | Blue |
| Alkaline Phosphatase | Naphthol-AS-BI-phosphate/fast red TR | NABP/ FR | Clear | Red |
| | Naphthol-AS-MX-phosphate/fast red TR | NAMP/ FR | Clear | Red |
| | Naphthol-AS-BI-phosphate/new fuchsin | NABP/ NF | Clear | Red |
| | Bromochloroindolyl phosphate/nitro-blue tetrazolium | BCIP/ NBT | Clear | Purple |
| | 5-Bromo-4-chloro-3-indolyl-B-d-galactopyranoside | BCIG | Clear | Blue |
| B-Galactosidase | Naphthol AS-BI-B-d-galactopyranoside | NABG | Clear | Red |

Generally, the color produced is proportional to the amount of unknown in the sample, providing the unknown is the limiting component of the system. The BCIP,NBT Phosphates Substrate System generates a dark purple strain on membrane sites bearing phosphatase. Alkaline phosphatase catalyzes the dephosphorylation of 5-bromo-4-chloro-3-indolyl phosphate which initiates a reaction cascade resulting in intense color formation.

Binding of an antibody can be detected by a variety of reagent systems as is the case for antigen bound to the antibodies of the membrane. For instance, 125 I-labelled antimouse immunoglobulin or 125 I-labelled protein A may be used. Antimouse immunoglobulin conjugated directly to alkaline phosphatase or to peroxidase may be used, together with appropriate chromogenic substrates. The biotin-avidin peroxidase system can be used together with appropriate chromogenic substrates. The biotin-avidin peroxidase system (for example, the Vectastain ABC system supplied by Vector Laboratories) is particularly sensitive.

The prefered membrane used in the invention is Gelman Supor membrane. Supor membrane is a low protein binding polysulfone membrane with a hydrophilic surface, superior flow rate, and particle retention. Gelman Supor Membranes provides a smooth surface, brilliant whiteness and opaqueness to enhance signal contrast in diagnostic tests, low extractables reduce sample contamination, uniform porosity ensures final product consistency, and no external wetting agent which prevents the introduction of unwanted extractables. These performance characteristics of Supor make it desirable for the inventive device.

While the solid phase membranes 14 eliminate handling, allow the product configuration to be cut in the desired shape or format for placement on a base, and provide faster kinetics and increased protein binding, protein binding to solid plastic substrates has been found to be a non-stoichiometric process and varies greatly with the type of plastic used. Binding is not specific and generally occurs through electrostatic and hydrophobic interreactions between plastic and proteins. Membrane substrates overcome many of the problems inherent in solid phase immunoassays as they combine the qualities of a solid substrate with a range of expanded capabilities and, due to their porosity and consequential large surface area, have a high protein binding capacity. Protein binding capacity is increased by using smaller pore sized membranes whose total binding surface increases for an equivalent frontal surface.

Membranes which can be used in the present invention, in addition to the noted latex, can be constructed of nitrocellulose, nylon, cellulose or IAM produced by Millipore Inc. The choice of adsorbing matrix depends on the physical properties such as sensitivity, binding capacity, stability or bound molecules and compatibility with the assay system.

Membranes, such as nylon and cellulose, can be modified to create surface sites for covalent binding of proteins. Nitrocellulose is one of the most commonly used membranes due to its high affinity for proteins and cellular macromolecules. In IAM, polyvinylidenedifluoride (PVDF), the base polymer of IAM, is hydrophobic and binds proteins. IAM permits a high degree of control over the extent of protein binding and the user can reproducably immobilize nanogram to microgram quantities of protein on the surface to suit various assay requirements. Binding the protein to IAM surfaces occurs primarily though the epsilon amino group of lysine, which contrasts the binding proteins to nitrocellulose, nylon or plastic where the bonding is ionic or hydrophobic.

Another type of membrane which can be used in the invention which has previously been noted is nitrocellulose which provides an excellent matrix for blotting proteins and nucleic acids. The nitrocellulose may be cut into whatever shape is required and has the useful characteristic that the amount of protein in a fingerprint will be clearly visible. Pure nitrocellulose adsorbs proteins, nucleic acids and other cellular antigens. These adsorbed substances often retain antigen-antibody binding activity and can be visualized using ultrasensitive, enzyme amplified immunostaining methods so that a chromogenic stain marks the location of the adsorbed materials. This approach uses a technique called Dot ELISA, (which also can be utilized with the Nylon, IAM, plastic membranes) whereby nanogram amounts of protein are directly applied to nitrocellulose. One important advantage of Dot ELISA is the ability to perform multiple enzyme immunoassays in a single test procedure using as little as one microliter of antigen or capture antibody solution. Nanogram amounts of capture antibodies dotted onto a single membrane can be used to screen simultaneously for a variety of antigens. In a Dot ELISA procedure the reactant is diluted in coating solution and dotted onto the damp membrane. While the optimal concentration will vary from reactant to reactant, for complex antigens 0.1–1.0 mg/ml is suitable. Following membrane blotting excess binding sites are blocked by thoroughly soaking both sides of the membrane in Diluent/Blocking Solution. Any of a variety of reservoirs can be used. The Diluent/Blocking Solution contains 1% bovine serum albumin (BSA) in phosphate buffered saline which protects adsorbed protein from surface denaturation. Following the blocking step, membranes can be stored dry at refrigeration temperatures for several months without loss of activity. The adsorption of an antigen or capture antibody onto the nitrocellulose membrane can be accomplished by Antigen Detection ELISA, Indirect Antibody ELISA (which is capable of detecting either antibody or antigen, depending on which is defined as the unknown) or Antibody Sandwich ELISA which is accomplished by adsorption of an antigen or capture antibody, washing each reagent of any free or unattached reactant and adding another reagent to build step by step a molecular sandwich on the membrane surface which is completed by the addition of an enzyme-antibody conjugate. The construction of such membrane surfaces is clearly shown by a bulletin of Kirkegaard & Perry Laboratories, Inc. 1985 entitled ELISAmate (TM) Enzymne Immunoassay Test System for Detection of Antigens or Antibodies on Membranes which is incorporated in this application by reference.

Figure 5:
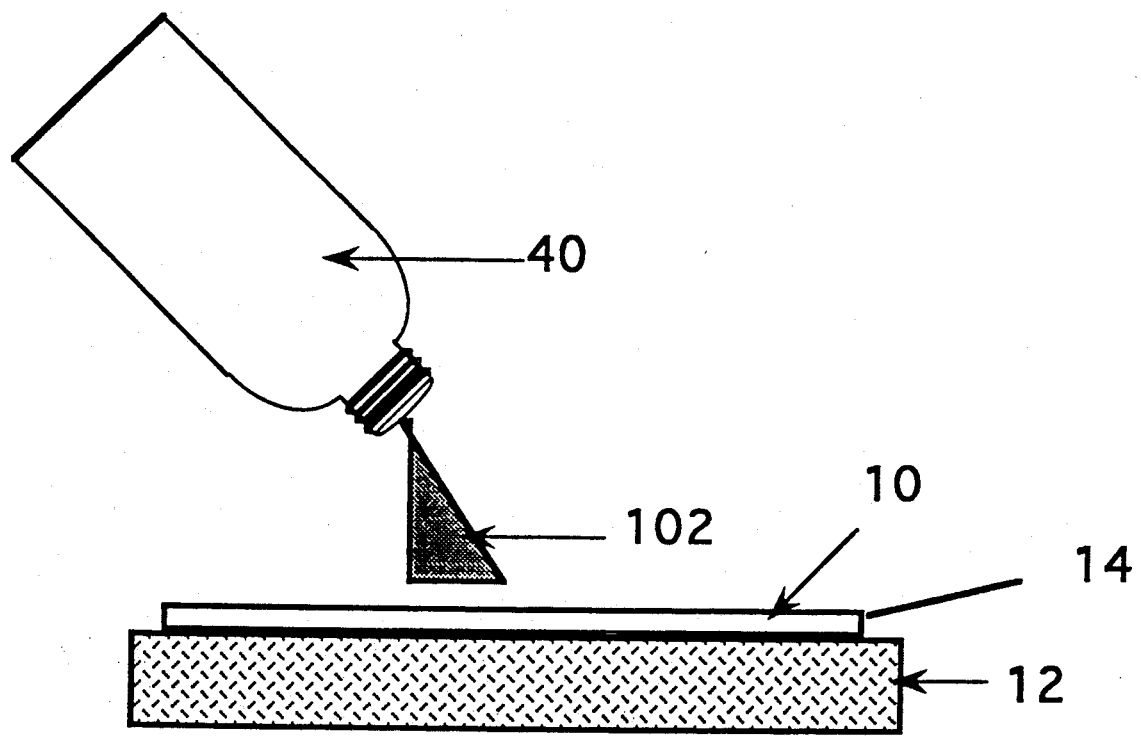
FIG. 5 is a schematic cross sectional representation showing addition of the composite sample of FIG. 4 to the center of the fingerprint pad.
Figure 6:
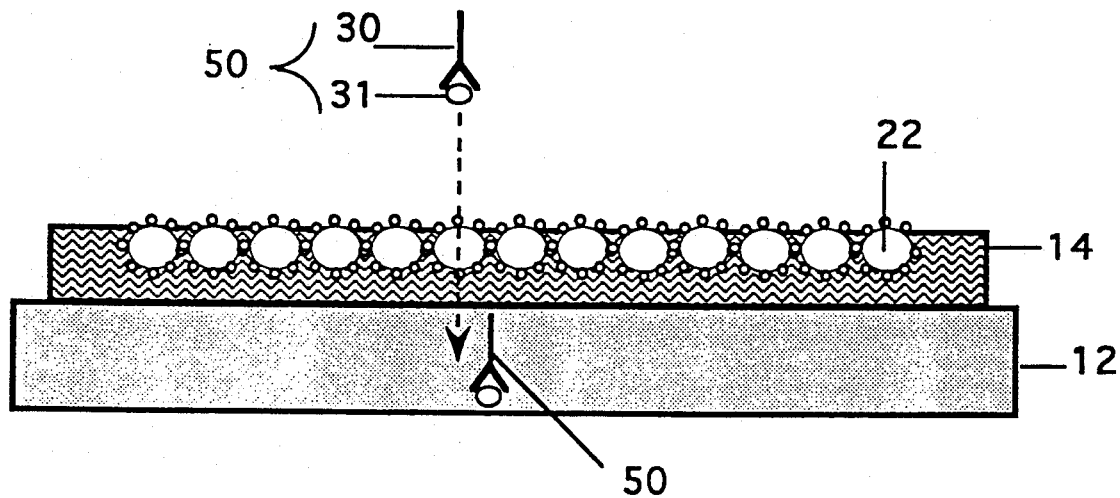
FIG. 6 is an enlarged schematic cross sectional view taken across a test area of the fingerprint pad of the pre invention illustrating the presence of antigen in the composite sample of FIG. 4 showing that antigen coated particles embedded in the membrane in the test areas will not capture the antibody.
Figure 9:
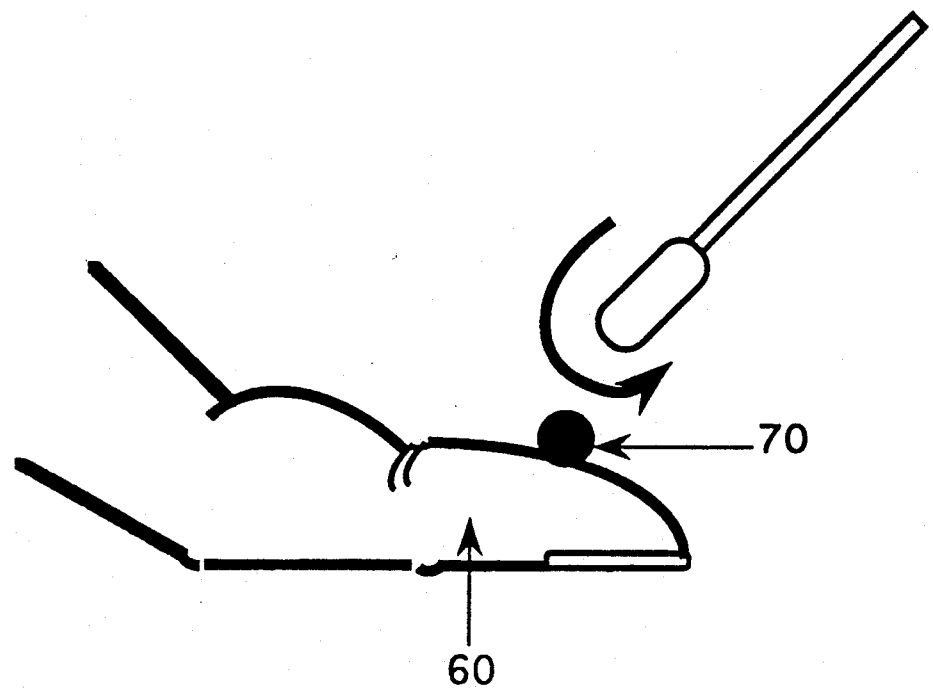
FIG. 9 is an enlarged schematic representation showing the painting of the test subject's finger with goat anti-mouse antibody labelled with colloidal gold.
Figure 10:
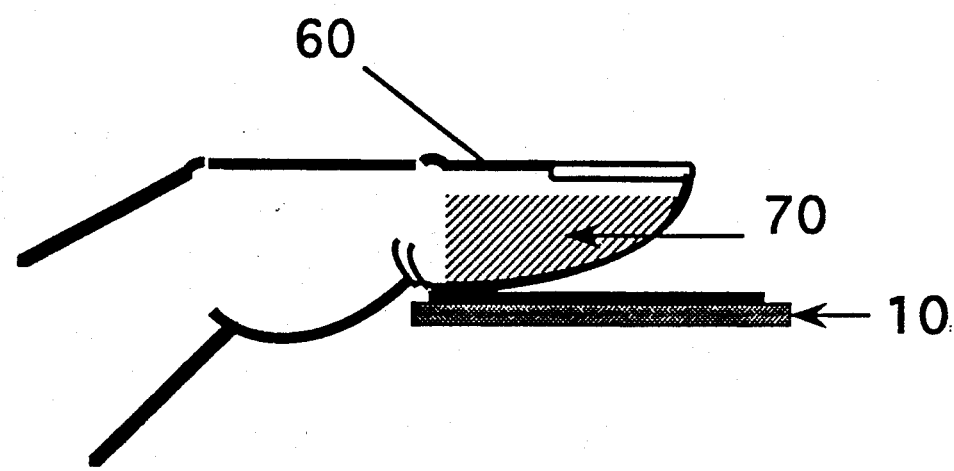
FIG. 10 is a schematic representation showing the painted finger of FIG. 9 lightly pressed against the previously immersed finger print pad membrane.
Figure 11:
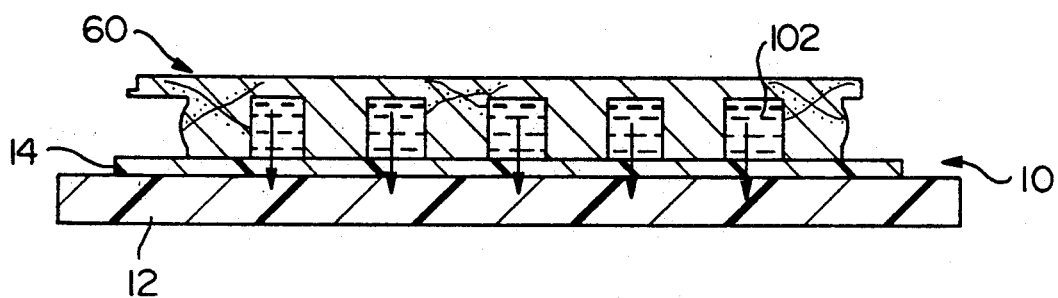
FIG. 11 is an enlarged schematic cross sectional representation of the fingerprint whorl extrusions coated with antibody labelled with colloidal gold pressed down on the solution saturated membrane of the fingerprint pad.
Figure 14:
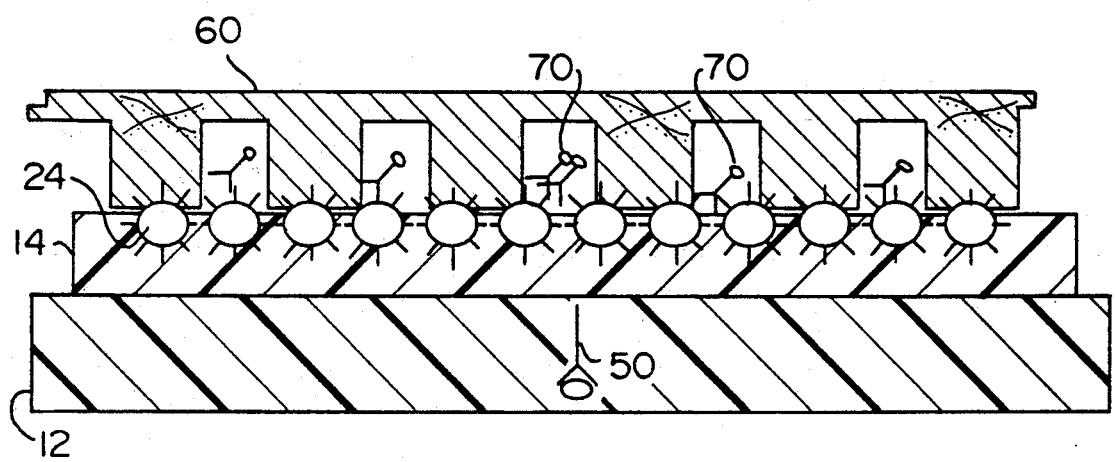
FIG. 14 is an enlarged schematic cross sectional representation across a control area of the finger pad of the present invention following FIG. 11 where the colloidal gold goat anti-mouse antibody is captured by the mouse anti-goat coated particles embedded in the membrane.

In operation of the inventive testing method, the body fluid test sample 100 is mixed with unlabelled primary mouse anti-antigen antibodies 30 and incubated in container 40 for three (3) minutes as schematically shown in FIG. 4. The entire mixed sample 102 is deposited on the center of the fingerprint pad 10 as shown in FIG. 5, incubated for about 1 to 3 minutes, preferably two (2) minutes, and drained. The ligand capture or non-capture after the incubation has been previously discussed. A washing solution (not shown) is added to the membrane surface 14 of the fingerprint pad and allowed to drain. The finger 60 of the subject is painted with 20 microliters goat anti-mouse antibody labelled with colloidal gold as shown in FIG. 9. The finger 60 is then pressed against the plastic membrane 14 and held for 5 seconds against membrane 14 and then removed If designated antigen 32–37 is present in the test sample 100, the complexed mouse antibody/antigen 50 and colloidal gold goat anti-mouse antibody 70 will pass through the test areas 20 of the membrane 14 into the porous plastic absorbent pad 12 (as shown in FIG. 12). If designated antigen 32–37 is absent in the sample, the colloidal gold goat anti-mouse antibody 70 is captured by the mouse antibodies 30 which were previously captured in turn by the antigen coated particles 22 of the test areas 20 in the membrane 14 (FIG, 13). In the control areas 16 and 18 of the membrane 14, as shown in 14, the colloidal gold goat anti-mouse antibody 70 is captured by the mouse anti-goat antibody coated particles 24 embedded in the membrane 14. This capture will give the fingerprint 62 swirls and whorls as is clearly shown in FIG. 15. It should be noted that the test result for positive analytes is different in that there is no coloration, while the negative areas show color. This coloration of negative test areas and lack of coloration of positive test areas is used to prevent the subject being tested from reading the test results after the fingerprint has been made in that one normally assumes that a coloration test indicates positive, rather than a lack of color.

EXAMPLE

In this example of Latex Entrapment with Colloidal Gold Labelled Antibodies as the color substrate, antibodies and antigens bound to latex spheres were entrapped on the surface of a membrane. The membrane must be low non-specific protein binding, and must have a smooth surface with consistent porosity.

I. MATERIALS/REAGENTS

1-Device: SUPOR 800 Laminate on Screen pattern
2-Latexes: 0.6 um IDC polystyrene latex (PSL) coated with goat anti-mouse IgG (absorbed against human serum) and HSA-benzoylecgonine (HSA-BE).
3-Colloidal gold conjugate: 20 nm or 40 nm colloidall gold conjugated with goat anti-mouse IgG (human absorbed).
4-Mouse anti-benzoylecgonine monoclonal antibody.
5-Blocking/wash buffer: PBS+2% PVA (10K)+1% Glycine+0.05% Tween-20.
6-Monoclonal antibody diluent: PBS+0.1% BSA+0.05% Tween-20.
7-Colloidal gold conjugate diluent: TRIS+1% BSA+0.05% Tween-20+0.05% Azide.
8-PSL diluents: Goat anti-mouse IgG(PBS+4% Sucrose+1% BSA+0.05% Azide); HSA-BE (0.2M sodium bicarbonate).

II-PREPARATION OF ASSAY DEVICE

1-Add 400–500 ul of blocking buffer.
2-Spot 40 ul of goat anti-mouse IgG PSL (1/16 dilution) into central well and 2 ul of HSA-BE PSL (¼ to 1/16) dilution in the appropriate number of test wells.
3-Invert on hydrophobic PE and dry for at least one hour in a drying room set at between 80 and 100 F.

III-ASSAY PROCEDURE

1-Obtain saliva sample using a BioQuant device.
2-Into SQ-Easy tube add 200 ul of saliva sample and 200 ul of mouse anti-BE IgG at 1/400 to 1/1600 dilution.
3-Incubate for 3 minutes.
4-During the sample incubation, add 400 ul of blocking solution to device and let drain.
5-After sample incubation, add 400 ul of sample to the device.
6-Incubate for 2 minutes.
7-Add 400 ul of blocking/wash buffer, let drain.
8-Paint thumb with 15 ul of goat anti-mouse IgG gold conjugate. Note: Don't paint thumb until wash buffer has drained into the reservoir.
9-Gently press thumb against the device and hold for 3 to 5 seconds and then carefully roll the thumb to the left and the device.
10-Incubate for 15 seconds and add 400 ul wash buffer.
11-Carefully remove the membrane from the device.

In the foregoing description, the invention has been described with reference to a particular preferred embodiment, although it is to be understood that specific details shown are merely illustrative and the invention may be carried out in other ways without departing from the true spirit and scope of the following claims:

What I claim is:

1. A method for testing for analytes in a body fluid of a test subject and positively identifying said test subject by producing a fingerprint of said test subject comprising the steps of:

(a) obtaining a quantity of body fluid from said test subject;

(b) combining anti-analyte antibodies which specifically bind to said analytes with said body fluid to form a solution whereby said anti-analyte antibodies specifically bind to said analytes if present therein;

(c) applying said solution to the membrane of a test device, said membrane comprising a control zone for recording a fingerprint of said test subject, said control zone having anti-species antibody immobilized thereon that specifically binds labelled antibody added as the detection antibody and test zones for determining the presence of said analytes, said test zones having antigens immobilized thereon that specifically bind to said anti-analyte antibodies wherein said solution contacts said control and test zones and wherein said anti-analyte antibodies not bound in step (b) bind to said antigens immobilized in said test zones;

(d) coating a finger of said test subject with labelled antibody which specifically binds to said anti-analyte antibodies and said anti-species antibody; and (e) placing the coated finger onto said membrane of said test device thereby contacting said control and test zones wherein a fingerprint of said test subject is produced in said control area and wherein said labelled antibody binds to said anti-analyte antibodies bound in said test areas, the presence of said labeled antibody indicating the absence of said analytes in said body fluid and the absence of said labeled antibody indicating the presence of said analytes in said body fluid.

2. The method of claim 1 wherein said antigens are immobilized as antigen coated particles.

3. The method of claim 1 wherein said labelled antibody is labelled with colloidal gold.

4. The method of claim 1 wherein said labelled antibody is labelled with a fluorescent label.

5. The method of claim 1 wherein said anti-analyte antibodies are mouse anti-analyte antibodies.

6. The method of claim 1 wherein said labelled antibody is labelled goat anti-mouse antibody.

7. The method of claim 1 wherein said body fluid is saliva.

8. The method of claim 1 wherein said body fluid is blood.

9. The method of claim 1 wherein said body fluid is urine.

10. The method of claim 1 wherein said anti-species antibody is mouse anti-goat antibody.

11. A method as claimed in claim 1 wherein said analyte is a drug.

12. A method as claimed in claim 1 wherein said analyte is cocaine.

13. A method as claimed in claim 1 wherein said analyte is PCP.

14. A method as claimed in claim 1 wherein said analyte is THC.

15. A method as claimed in claim 1 wherein said analyte is methamphetamine.

16. A method as claimed in claim 1 wherein said analyte is alcohol.

17. A method as claimed in claim 1 wherein said analyte is opiate.

18. A method for testing for drugs or metabolites thereof in a human body fluid and simultaneously positively identifying the test subject from whom said body fluid is collected by producing a fingerprint of said test subject comprising the steps of:

(a) mixing said body fluid collected from said test subject with anti-drug or anti-drug metabolite antibodies specific for said drugs or said metabolites thereof to form a composite solution wherein said anti-drug or anti-drug metabolite antibodies specifically bind to said drugs or said metabolites thereof respectively if present in said body fluid;

(b) covering the surface of a membrane of a test device with said composite solution, said surface of said membrane comprising a control zone for recording said fingerprint of said test subject, said control zone having immobilized thereon anti-species antibody that specifically binds labelled antibody added as the detection antibody and test zones for determining the presence of said drugs or metabolites thereof, said test zones having immobilized thereon antigens that specifically bind to said anti-drug or anti-drug metabolite antibodies;

(c) allowing said solution to incubate on said surface of said membrane for a specific period of time so that said anti-drug or anti-drug metabolite antibodies not bound in step (a) bind to said antigens immobilized in said test zones;

(d) coating a portion of a finger of said test subject with labelled antibody which specifically binds to said anti-drug or anti-drug metabolite antibodies and said anti-species antibody; and (e) pressing said finger against said control and test zones on said surface of said membrane to deposit said labelled antibody onto said surface wherein a fingerprint is produced in said control zone and wherein said labelled antibody binds to said anti-drug or anti-metabolite antibodies bound in said test zones, the presence of said labeled antibody in said test zones indicating the absence of said drugs of metabolites thereof in said body fluid and the absence of said labeled antibody in said test zones indicating the presence of said drug or metabolic breakdown product thereof in said body fluid.

19. The method of claim 18 wherein said drug are selected from the group consisting of opiates, barbiturates, antipsychotics, antidepressants, analgesics, sedatives, hypnotics, benzodiazepines, solvents, stimulants, hallucinogens and anabolic steroids.

20. The method of claim 18 wherein said composite solution incubated in step (c) is incubated for at least two minutes.

21. The method of claim 18 wherein said composite solution incubated in step (c) is incubated for one to three minutes.

22. The method of claim 18 wherein said finger is pressed against said membrane surface for about 5 seconds.

23. The method of claim 18 wherein said labelled antibody is labelled with colloidal gold.

24. The method of claim 18 wherein the label of said labelled antibody comprises gold particles coated with silver.

25. The method of claim 18 wherein said anti-drug or anti-drug metabolite antibodies are mouse anti-drug or mouse anti-drug metabolite antibodies.

26. The method of claim 18 wherein said labelled antibody is labelled goat anti-mouse antibody.

27. The method of claim 18 wherein said body fluid is saliva.

28. The method of claim 18 wherein said body fluid is blood.

29. The method of claim 18 wherein said body fluid is urine.

30. The method of claim 18 wherein said anti-species antibody is mouse anti-goat antibody.

31. The method of claim 18 further comprising washing said membrane surface after step (c).

32. A method of testing for drugs or metabolites thereof in a body fluid of a test subject and also positively identifying said test subject from whom said body fluid is collected by producing a fingerprint of said test subject comprising the steps of:
  (a) mixing said body fluid taken from said test subject with anti-drug or anti-drug metabolite antibodies specific for said drugs or metabolites thereof respectively to form a composite solution wherein said anti-drug or anti-drug metabolite antibodies specifically bind to said drugs or metabolites thereof respectively if present in said body fluid;
  (b) covering the surface of a membrane of a pad assembly, such pad assembly comprising said membrane mounted on an absorbent pad, with said composite solution, said surface comprising a control zone for recording said fingerprint of said test subject, said control zone having anti-species antibody immobilized thereon that specifically binds labelled antibody added as the detection antibody and test zones for determining the presence of said drugs or metabolites thereof, said test zones having immobilized thereon antigens that specifically bind to said anti-drug or anti-drug metabolite antibodies;
  (c) allowing said composite solution to incubate on said surface of said membrane for at least one minute wherein said anti-drug or anti-drug metabolite antibodies not bound in step (a) bind to said antigens immobilized in said test zones;
  (d) applying to a finger of said test subject a coating of labelled antibody which specifically binds to said anti-drug or anti-drug metabolite antibodies and said anti-species antibody;
  (e) pressing said finger of said test subject against said control and test zones on said surface of said membrane for 2-10 seconds to deposit labelled antibody onto said surface of said membrane wherein a fingerprint of said test subject is produced in said control zone and wherein said labelled antibody binds to said anti-drug or anti-drug metabolite antibodies bound in said test zones, the presence of said labelled antibody indicating the absence of said drugs or metabolites thereof in said body fluid and the absence of said labeled antibody indicating the presence of said drugs or metabolites thereof in said body fluid.

33. The method of claim 32 wherein said drugs are selected from the group consisting of opiates, barbiturates, antipsychotics, antidepressants, analgesics, sedatives, hypnotics, benzodiazepines, solvents, stimulants, hallucinogens and anabolic steroids.

34. The method of claim 32 wherein said anti-drug or anti-drug metabolite antibodies are mouse anti-drug or anti-drug metabolite antibodies.

35. The method of claim 32 wherein said labelled antibody is labelled goat anti-mouse antibody.

36. The method of claim 32 wherein said labelled antibody is labelled with colloidal gold.

37. The method of claim 32 wherein said labelled antibody is labelled with a fluorescent label.

38. The method of claim 32 wherein said body fluid is saliva.

39. The method of claim 32 wherein said body fluid is blood.

40. The method of claim 32 wherein said body fluid is urine.

41. The method of claim 32 wherein said anti-species antibody is mouse anti-goat antibody.

42. The method of claim 32 further comprising washing said surface of said membrane after step (c).

43. A method for positively identifying a test subject by producing a fingerprint of said test subject comprising the steps of:
  (a) coating a finger of said test subject with labelled antibody which specifically binds to anti-species antibody immobilized on the surface of a membrane mounted on an absorbent pad of a test device; and
  (b) pressing said finger of said test subject against said surface of said membrane having immobilized thereon said anti-species antibody which specifically binds to said labelled antibody and thereby contacting said labelled antibody with said anti-species antibody immobilized on said surface of said membrane to produce a fingerprint of said test subject on said surface of said membrane.

* * * * *